United States Patent [19]

Burgin

[11] Patent Number: 4,697,578
[45] Date of Patent: Oct. 6, 1987

[54] ACRYLOOPTIC TONGUE DEPRESSOR AND HANDLE THEREFOR INCORPORATING ADJUSTABLE VIEWING OPTICS

[76] Inventor: Kermit H. Burgin, R. R. #1, Box 334, Whitestown, Ind. 46075

[21] Appl. No.: 482,864

[22] Filed: Apr. 7, 1983

Related U.S. Application Data

[63] Continuation of Ser. No. 284,484, Jul. 17, 1981, abandoned.

[51] Int. Cl.⁴ ............................................. A61B 1/06
[52] U.S. Cl. ..................................................... 128/16
[58] Field of Search ..................................... 128/6–16; 350/251, 252, 419

[56] References Cited

U.S. PATENT DOCUMENTS

| | | | |
|---|---|---|---|
| 2,023,945 | 12/1935 | Allyn | 128/16 |
| 2,244,568 | 6/1941 | Palmeter | 128/6 |
| 2,648,329 | 8/1953 | Morch | 128/11 |
| 3,224,437 | 12/1965 | Hardgrove | 128/9 |
| 3,778,134 | 12/1973 | Welham | 353/5 |
| 3,916,881 | 11/1975 | Heine | 128/16 |
| 4,037,588 | 7/1977 | Heckele | 128/11 |
| 4,320,745 | 3/1982 | Bhitiyakul et al. | 128/11 |

FOREIGN PATENT DOCUMENTS 2302614   7/1974   Fed. Rep. of Germany ........ 128/15

Primary Examiner—Kyle L. Howell
Assistant Examiner—Max F. Hindenburg
Attorney, Agent, or Firm—Barnes & Thornburg

[57]   ABSTRACT

A combination handle unit and tongue depressor includes a light source, a means for attaching a light-transmissive disposable depressor member to the handle to conduct light from the source into, for example, the mouth and throat of a patient being examined, and an adjustable lens which can be focussed into the illuminated area for viewing. The lens is mounted on the handle unit for sliding movement back and forth to change the focal plane so that different depths of the region being examined can be brought into clear focus.

6 Claims, 4 Drawing Figures

U.S. Patent    Oct. 6, 1987    4,697,578
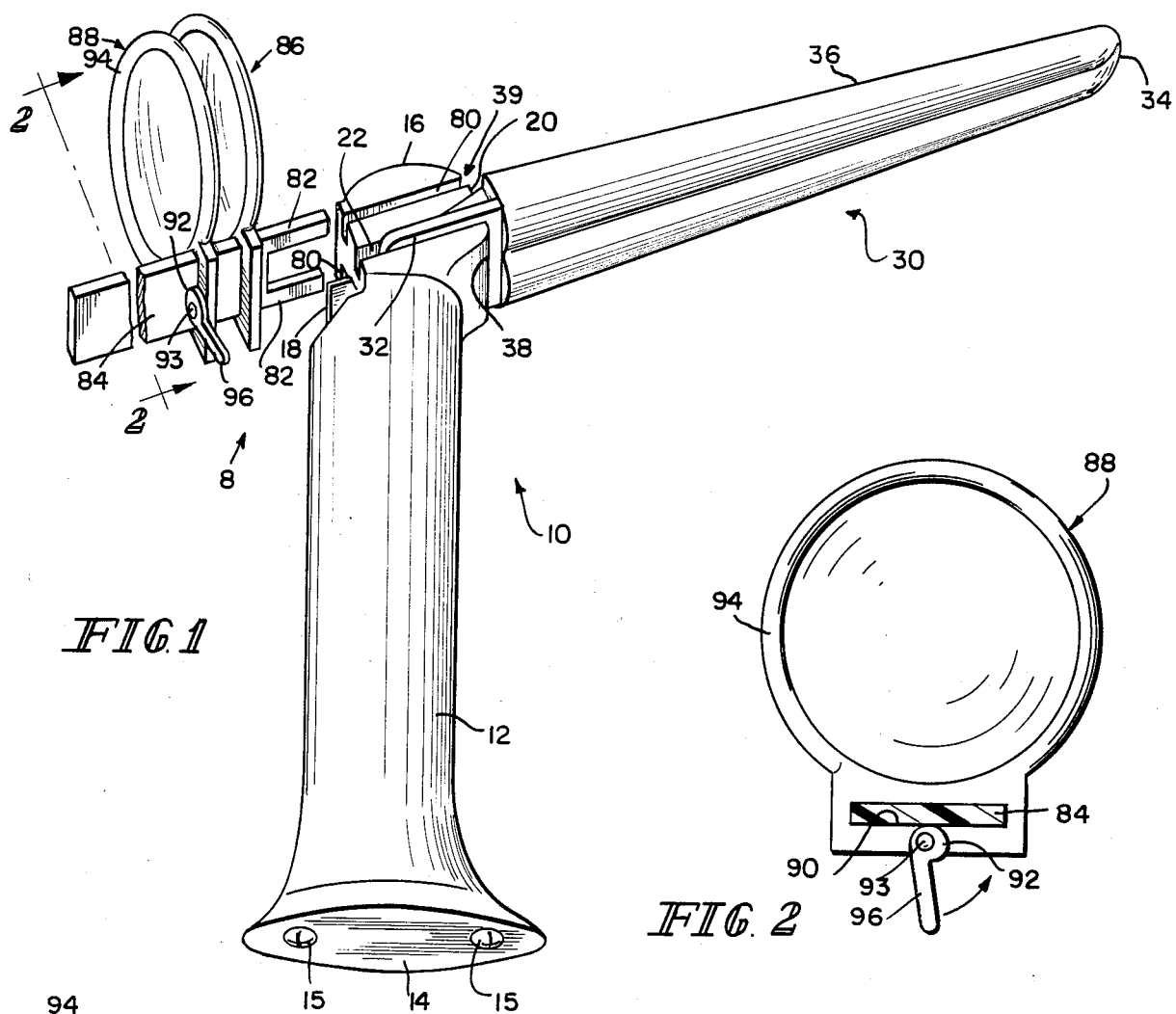
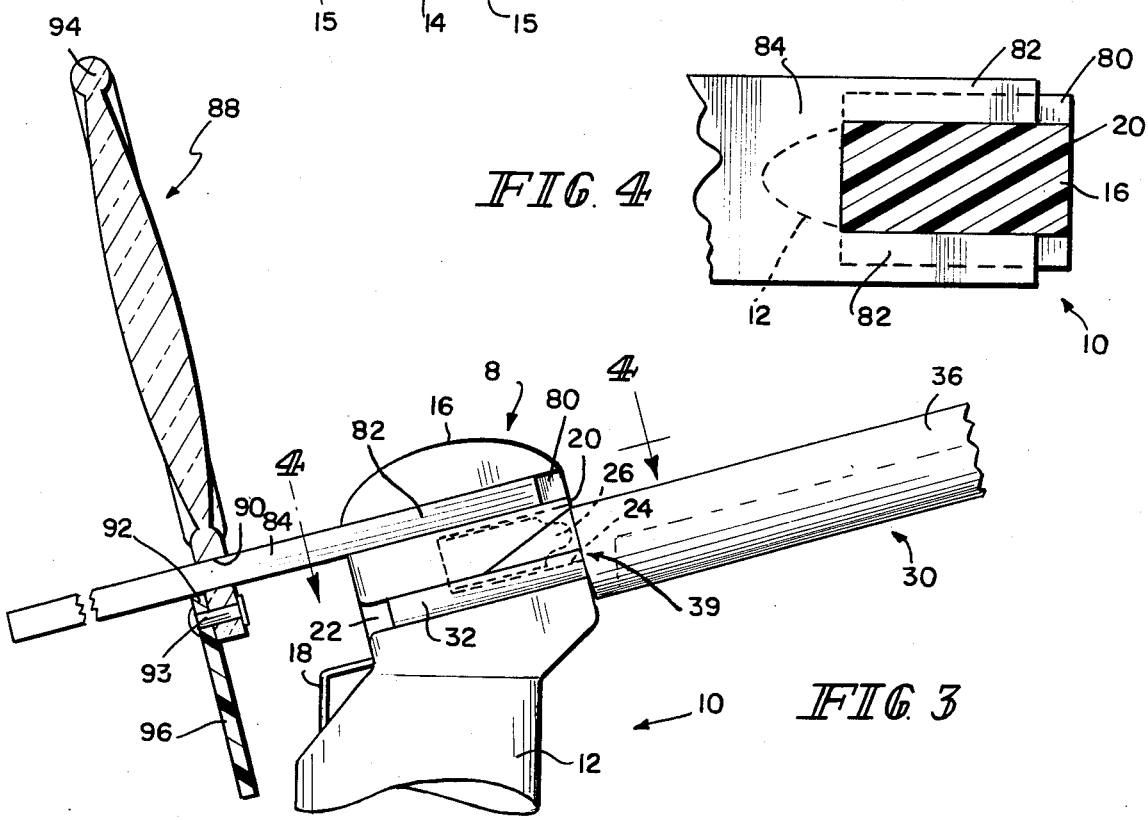

ACRYLOOPTIC TONGUE DEPRESSOR AND HANDLE THEREFOR INCORPORATING ADJUSTABLE VIEWING OPTICS

This is a continuation of application Ser. No. 284,484, filed July 17, 1981, now abandoned.

This is a related application to my application Ser. No. 958,795, filed Nov. 8, 1978, which is a continuation-in-part of my application Ser. No. 811,550, now U.S. Pat. No. 4,165,746; my application Ser. No. 958,794, now U.S. Pat. No. 4,263,899, which is a continuation-in-part of my application Ser. No. 901,521, now U.S. Pat. No. 4,156,424; my application Ser. No. 10,751, filed Feb. 9, 1979, now abandoned; my application Ser. No. 180,352, filed Aug. 22, 1980, which is a continuation of Ser. No. 10,751; and my application Ser. No. 105,509, filed Dec. 20, 1979.

This invention relates to medical examination instruments, and specifically to tongue depressors and the like.

In the past, when examining the mouth, throat, and surrounding tissues, it has been customary to depress the tongue with a depressor held in one hand and to illuminate the mouth and throat of a patient with a light source held in the other hand. Aside from the awkwardness of requiring both hands, the apparatus of the prior art requires that the light source be held close to the examiner's line of sight, or even that the examiner look through an aperture provided in an examining instrument containing the light source.

Various types of medical examination instruments utilizing fiber optic or acrylooptic light transmission to illuminate a body orifice, meatus, or incision for examination or the like, are known. There are, for example, the disclosures of the following U.S. Pat. Nos.: 3,664,330; 3,762,400; 3,796,214; 3,716,047; 3,890,961; 2,247,258; 4,086,919; 3,851,642; 3,592,199; 3,324,850; 3,131,690; 2,482,971; and 3,978,850.

Attention is specifically directed to German Offenlegungsschrift No. 2,302,614 and U.S. Pat. Nos. 2,690,745; 3,890,960; and 3,916,881.

Briefly, the invention comprises an examination instrument having a handle, an examination member, and means for coupling the examination member to the handle. The illustrative examination instrument is constructed from some light-transmissive material, such as an acrylic-styrene mixture (acrylic material for light-transmission characteristics, styrene for strength), for use with a combination handle and light source unit. Such a depressor is constructed so that light from the source is directed through the light-transmissive material of the depressor and is adapted at a proximal end to be attached to such handle unit. A viewing lens, illustratively one having an adjustable depth of field, is mounted on the handle so that the illuminated region can be viewed. In the illustrative embodiments, the illuminated region can be selectively focussed at different depths and viewed.

In one of the illustrative embodiments, the viewing system includes two lenses which cooperate. One of the lenses is relatively fixed and the other is relatively movable to adjust the depth of field as desired.

The invention may be best understood by reference to the following description and accompanying drawings which illustrate the invention. In the drawings:

FIG. 1 is a perspective view of an apparatus constructed according to the invention;

FIG. 2 is a sectional view of a detail of the apparatus of FIG. 1, taken generally along section lines 2—2 thereof;

FIG. 3 is a partly sectional, fragmentary side elevational view of another apparatus constructed according to the invention; and FIG. 4 is a fragmentary sectional view of a detail of the apparatus of FIG. 3, taken along section lines 4—4 thereof.

Referring to FIG. 1, a medical examination instrument 8 includes a base 10 having a somewhat tubular handle 12, a bottom cap 14 held on by screws 15, and a head 16. Handle 12 serves to hold one or more batteries (not shown) which provide a power source. If an alkaline battery is used, the battery can be molded into the handle 12 which will have a useful life of up to six months and a shelf life of up to five years. A switch 18 controls delivery of power from the batteries. Head 16 is provided with a forwardly extending face 20 and a groove 20 which extends perimetrally about both sides and across the face 20 of head 16.

Referring now to FIG. 3, head 16 provides a socket 24 which receives an electric light bulb 26. Conductors, which illustratively are molded into the plastic material from which head 16 is formed, supply power through switch 18 from the batteries to bulb 26.

As may be seen in both FIG. 1 and FIG. 3, a member 30, shown in a form suited for use as a tongue depressor, has a proximal end 32 and a downwardly turned and slightly concave distal end 34. Different concavities, curvatures, etc., can be provided so that an examining physician can select a member 30 to meet the requirements of a specific examination. A beaded (e.g., flame-treated) edge 36 is provided about the perimeter of member 30 except along the edge of proximal end 32. A notch 38 is provided in the edge of proximal end 32 to clear the bulb enclosure portion 39 of head 16 so that member 30 can be inserted into groove 22 of head 16 where it will be frictionally retained.

Head 16 can be constructed from an opaque plastic material and can be provided with highly reflective surfaces, especially those surfaces in contact with member 30 and the surface of face 20. Such surfaces can be, for example, metal plated to provide mirror-like reflective surfaces. Member 30 should be made of a light-transmissive material such as a polymethylmethacrylate-styrene mixture, and is preferably quite inexpensively constructed so as to be disposable. To this end, member 30 is provided with a central reinforcing and light-concentrating rib 46. Rib 46 cooperates with the bead 36 to provide longitudinal stiffness to member 30. This permits the web regions 48 between the bead 36 and rib 46 to be made quite thin, conserving on the amount of material required to construct the members 30 to achieve a desired strength, and therefore reducing the cost of such members 30.

In accordance with the teachings of my above-identified U.S. patent application Ser. No. 10,751, a lens (not shown) for directing the light transmitted down rib 46 can be provided adjacent distal end 34 of member 30. To meet the specific requirements of a particular application, that lens can be made to focus or to diffuse the light to provide the necessary illumination in the mouth, throat, etc.

As can be seen in FIGS. 1 and 4, an additional pair of grooves 80 is provided on head 16 above groove 22. Grooves 80 are adapted for engagement by the fork-like protrusions 82 which exend forward from a flat, rectangular cross-section, plate-like slide member 84. Protrusions 82 snugly engage head 16 to prevent accidental disengagement.

In the embodiment of the invention illustrated in FIGS. 1 and 2, a viewing lens 86 is molded onto slide 84 to project above head 16. Since this lens 86 is molded to slide 84, its position is relatively fixed. Typically, lens 86 is a magnifying lens. An additional lens 88 is provided with a rectangular cross section opening 90 which permits it to be slid into position on slide 84. Lens 88 is provided with a cam-shaped friction locking device 92 which is pivotally mounted at 93 to the lens frame 94 beneath opening 90 and operated by a toggle lever 96. Lens 88 can be positioned along slide 84 by moving lever 96 clockwise from its position illustrated in FIG. 2, selectively repositioning lens 88, and then moving lever 96 counterclockwise back past the position illustrated in FIG. 2 to engage the raised lobe of the cam on device 92 frictionally with the underside of slide 84. Lens 88 typically also will be a magnifying lens, and lenses 86, 88 will be chosen such that they cooperate optically to provide a depth of focus somewhere within the orifice being examined by a physician manipulating contacting member 30.

In the embodiment illustrated in FIGS. 3 and 4, the stationary lens of FIGS. 1 and 2 is eliminated and the adjustable lens 88 alone is used. The adjustment of the depth of focus available with a single lens 88 can be sufficient to provide adequate adjustment of the focus, depending upon the characteristics of lens 88, the depth at which observation is being made, and the desired amount of magnification.

What is claimed is:

1. An examination instrument comprising a base unit having a handle portion providing a hand grip and a head portion, the head portion having peripheral surfaces including a first front surface and two side surfaces adjacent the front surface, a first pair of grooves, the grooves of the first pair disposed one on each of the two side surfaces, a second pair of grooves, the grooves of the second pair disposed one on each of the two side surfaces, an examination member having a distal end for contacting a body surface to be examined and a proximal end having a pair of members inserted into respective grooves of the first pair of grooves to removably attach the examination member to the base unit, the examination member having a top surface, a light source mounted in the base unit for providing light in the head portion of the base unit, the examination member being attached adjacent the light source, a viewing lens, and means for removably attaching the viewing lens to the base unit, the attachment means including a pair of members insertable into respective grooves of the second pair of grooves, the viewing lens providing a user with a line of sight above the top surface of the examination member.

2. The invention of claim 1 and further comprising a second viewing lens, means for attaching the second viewing lens to the base unit, the second viewing lens being cooperable with the first viewing lens to provide the desired view of the surface to be examined.

3. The invention of claim 1 wherein the means for attaching the viewing lens to the base unit further includes a slide portion, and the viewing lens includes a mounting portion having a slot for selectively movably engaging the slide portion.

4. The invention of claim 3 further comprising a cam means mounted on the mounting portion of the viewing lens, the cam means having a surface engageable with the slide portion selectively to prevent movement of the viewing lens along the slide portion.

5. An examination instrument comprising a base unit having a handle portion providing a hand grip and a head portion,
   the head portion having peripheral surfaces including a front surface and two side surfaces,
   a first pair of grooves disposed on the head portion, one on each of the side surfaces,
   a second pair of grooves disposed on the head portion, one on each of the side surfaces,
   an examination member having a distal end for contacting a body surface to be examined, and a proximal end having a pair of longitudinal members slidably inserted into the first pair of grooves for removably attaching the examination member to the head portion of the base unit,
   a first viewing lens mounted to a slide member, the slide member including a pair of longitudinal members slidably inserted into the second pair of grooves to removably attach the slide member to the head,
   a second viewing lens, and means for removably attaching the second viewing lens to the slide member, the second viewing lens being movable with respect to the first viewing lens to provide the desired view of the surface to be examined.

6. An examination instrument comprising
   a base unit having a handle portion providing a hand grip and a head portion,
   the head portion including a front surface and two side surfaces, each of the side surfaces including at least one groove,
   a light-trnsmissive examination member for contacting a body surface to be examined, means for attaching the examination member to the head portion of the base unit,
   a viewing lens,
   means for movably attaching the viewing lens to the base unit to permit selective adjustment of the focus of the lens to view the surface to be examined, the viewing lens attaching means comprising
   a slide member having a pair of longitudinal members for insertion into respective grooves of the pair of grooves of the side surfaces of the head portion, a portion for mounting the viewing lens,
   the viewing lens including a mounting portion having a slot, the mounting portion slidably received in the slot on the viewing lens, and
   a cam means mounted on the mounting portion of the viewing lens, the cam means including a surface selectively engageable with the slide member to position the viewing lens selectively along the slide member.

* * * * *